United States Patent [19]

James et al.

[11] Patent Number: 4,589,422
[45] Date of Patent: May 20, 1986

[54] ELECTROMAGNETIC MEDICAL APPLICATORS

[75] Inventors: James R. James, Swindon; Reginald H. Johnson, Malvern, both of England

[73] Assignee: National Research Development Corporation, London, England

[21] Appl. No.: 576,708

[22] Filed: Feb. 3, 1984

[30] Foreign Application Priority Data

Feb. 4, 1983 [GB] United Kingdom ............... 8303179
Apr. 11, 1983 [GB] United Kingdom ............... 8309776

[51] Int. Cl.⁴ .................................................. A61N 5/00
[52] U.S. Cl. ............................. 128/804; 343/700 MS; 343/787
[58] Field of Search ............... 128/804, 399; 219/10.55 R, 10.79, 10.81; 343/700 MS, 787

[56] References Cited

U.S. PATENT DOCUMENTS 3,811,128  5/1974  Munson ............................... 343/787
4,240,445  12/1980  Iskander et al. ..................... 128/804

OTHER PUBLICATIONS

Bahl et al., "Microstrip Loop Radiators..." Conf: 1981 IEEE MTT S. Int. Microwave Symp. Dig., Los Angeles, Ca., pp. 465–467, Jun. 15–19, 1981.
Bahl et al., "A New Microstrip Radiator..." IEEE Trans. on MTT, vol.–MTT-28, No. 12, Dec. 1980, pp. 1464–1468.

*Primary Examiner*—Lee S. Cohen
*Attorney, Agent, or Firm*—William R. Hinds

[57] ABSTRACT

An electromagnetic medical applicator for heating tissue comprises a patch resonator (1) on a substrate (4) of dielectric material backed by a ground-plane (3), and having a layer (7) of dielectric material overlying the resonator inter alia to effect impedance-matching to tissue, in which the substrate includes a volume of magnetic material (5) adjacent the maximum-current region of the resonator in order to reduce the length of the resonator at its resonant frequency.

14 Claims, 5 Drawing Figures

ELECTROMAGNETIC MEDICAL APPLICATORS

This invention relates to electromagnetic medical applicators, also known as transducers. Such devices have one use in the heating of tissues, either alone or together with radiotherapy or chemotherapy, in the treatment of cancer.

The physical size of electromagnetic devices in media other than air is a function of the effective relative permittivity ($\epsilon$) and relative permeability ($\mu$) of the medium, and is proportional to $1/\sqrt{\mu\epsilon}$. The use of this effect has been described in commonly assigned UK Patent Application No. 2122092A (U.S. application Ser. No. 499,544, filed May 31, 1983) for reducing the size of resonant microstrip patch radiators in medical applicators, using a substrate of such a medium. Since it is desirable that such applicators should be physically small in order to localise the heating, such reduction facilitates the use of lower frequencies, which are more penetrative of muscle tissue. Additionally, in order to reduce reflections at the applicator/tissue interface and promote the flow of electromagnetic radiation into the tissue, it is desirable that their respective wave impedances, $\sqrt{\mu/\epsilon}$, should be matched reasonably closely.

In order to take full advantage of the size-reduction effect, materials having $\epsilon$ and $\mu$ both effectively greater than unity are desirable for use as the electromagnetic medium. Such materials can be made by fusing together finely-divided constituents having $\epsilon > 1$ and $\mu > 1$; however, the present invention enables an equivalent effect to be obtained without having to fabricate such special mixed materials.

According to the present invention an electromagnetic medical applicator comprises:

a resonator spaced from a conducting plane by a layer of an electromagnetic medium comprising separate volumes of magnetic material and of dielectric material with magnetic material located adjacent that region of the resonator where in use the resonator current is a maximum, said magnetic material providing an improved path for the magnetic field associated with said current;

and a layer comprising at least dielectric material overlying said resonator.

The resonator may be a patch resonator on a solid substrate constituting the aforesaid medium and backed by a conducting ground-plane, with said magnetic material extending transversely to the polarisation direction of the resonator. With a half-wave patch resonator said magnetic material underlies the central region of the resonator, and with a quarter-wave patch resonator said magnetic material underlies one end of the resonator; the remainder of said substrate need comprise only dielectric material in each case. In the quarter-wave case, the resonator is electrically connected to the ground-plane at said one end of the resonator.

It is found that an effective $\mu$-value usefully greater than unity can be achieved by locating the magnetic material in separate volumes located as aforesaid, instead of mixing it uniformly throughout the substrate medium in expensive specially fabricated materials. This is apparently because the magnetic field in the substrate, due to the resonator current, exists primarily in the specified region. Hence also it is unnecessary to distribute separate volumes of magnetic material throughout the substrate; indeed although some magnetic material elsewhere might not unduly affect the operation of the invention, too much could be deleterious by effectively diluting the dielectric material.

The layer overlying the resonator may also comprise a separate volume of magnetic material located adjacent the same resonator regions. However, an overlying layer of this nature will usually not be worthwhile, since the overlying material contributes only a relatively small size-reduction effect, this effect being primarily contributed by the substrate.

The length and breadth of the substrate and overlying layer should exceed those of the resonator itself to accommodate the surrounding fields, but should not exceed about twice these dimensions or unwanted modes may be generated.

It is a function of the overlying layer to provide impedance-matching between the applicator and the adjacent tissue. For power to transfer efficiently from the resonator to a tissue load, either $\epsilon$ for the dielectric material in the substrate and overlying layers (assumed equal, as will normally be the case unless the substrate is much less than that of tissue, when this assumption will be less applicable) must approximately match that of tissue or, if $\epsilon$ for the material is much higher, an additional matching layer is desirably provided beyond the overlying layer. The value of $\epsilon$ for tissue depends on the frequency, and according to recent measurements varies from about 50 to 900 MHz to about 55 at 300 MHz, increasing to about 70 at 100 MHz. As discussed in the aforesaid UK Application No. 2122092A; suitable values of the wave-impedance of $\sqrt{1/\epsilon}$ of the overlying layer (with no magnetic material, ie $\mu = 1$) to give resonable matching are preferably not less than about ⅔, and not more than about 1.5 times, that of tissue at the operating frequency. In either case the thickness of the overlying layer is preferably sufficent to allow a far-field wave-pattern to form, suitably about $\lambda_o/6$ thick, where $\lambda_o$ is the wavelength in the medium of the overlying layer.

To enable the nature of the present invention to be more readily understood, attention is directed, by way of example, to the accompanying drawings wherein.

Figure 1:
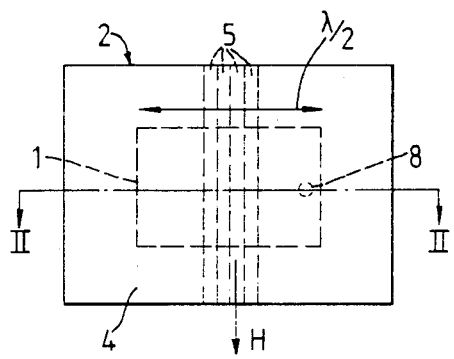
FIGS. 1 and 2 are respectively plan and cross-sectional views (on the line II—II in FIG. 1) of one embodiment of the present invention.
Figure 2:
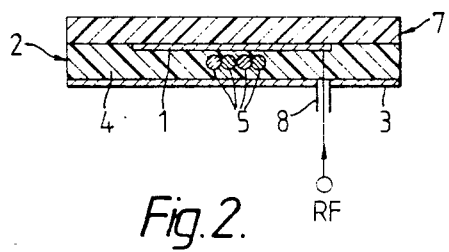

FIGS. 1 and 2 show a medical applicator comprising a copper half-wave path resonator 1 on a substrate 2 which comprises dielectric material 4 having four ferrite rods 5 inserted in holes therethrough below the central region of the patch as shown. A coaxial feed connection is shown at 8, having its inner conductor connected to the patch near one end and its outer conductor connected to a copper ground-plane 3 in a conventional manner, so that the resonator is polarised in the direction of the arrow marked $\lambda/2$. Overlying resonator 1 and substrate 2 is a layer 7 of the same dielectric material as substrate 2. The rods are aligned parallel to the magnetic field H of the resonator current which exists in the plane of the substrate, thereby most effectively providing improved paths for this field.

The rods 5 need not necessarily extend the full width of the substrate, nor necessarily be in line contact, nor be of circular section, as shown. For example, given the availability of suitable ferrite material of appropriate cross-section, the ferrite material may form a strip located between abutting slabs of dielectric material either side and of the same thickness, ie with no dielectric material below the central region of the patch.

In FIG. 1 the patch 1 is shown located in a recess in the substrate 2 so that there is no air-gap between the substrate and the overlying layer 7 beyond the patch periphery. Although not essential, this may be desirable where the patch 1 is of substantial thickness; alternatively the patch may not be recessed and the gap may be filled with material having a suitable value of $\epsilon$. It is important that the patch should be in intimate contact with both the substrate and the overlying layer. If the latter are not sufficiently flat to ensure this, similar metal patches can be applied to both with the two patches in back-to-back register. As mentioned earlier, the layer 7 may contain magnetic material above the central region of the patch 1 in order to further enhance the size-reduction effect, but the additional complication will usually not be worthwhile.

The half-wave patch resonator 1 need not be rectangular as shown; for example a circular patch of approximately half-wave diameter may be used to give greater bandwidth.

Figure 3:
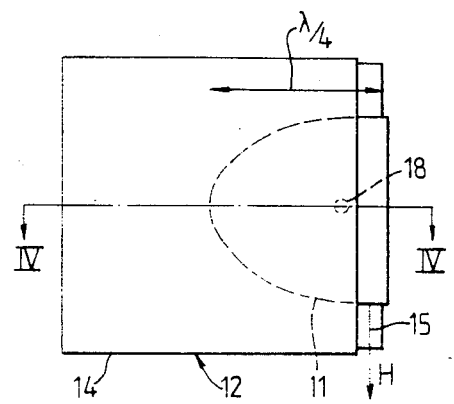
FIGS. 3 and 4 are corresponding views of another embodiment of the invention.
Figure 4:
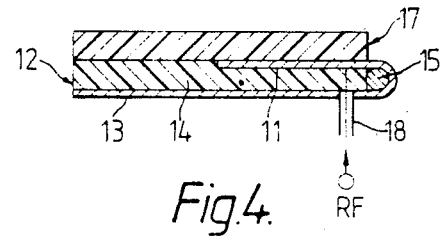

FIGS. 3 and 4 show a transducer using a quarter-wave patch resonator. The resonator 11 is formed of copper foil recessed into the upper surface of dielectric material 14, continuing round one end thereof, and round an abutting ferrite rod 15, to form the ground-plane 13. The material 14 and rod 15 together form the substrate 12 for the resonator 11, which is fed by a coaxial feed 18 at a point adjacent rod 15 and on the voltage antinode side of it. As in FIGS. 1 and 2, the rod 15 is seen to underlie that part of the resonator 11 where the current is a maximum. Instead of using a circular rod 15, the magnetic material may be a square- or rectangular-section strip, and need not necessarily have the same thickness as the material 14. Also, this magnetic material may be recessed into the end face of the dielectric material 14.

The profile of the resonator 11 is shown shaped in FIG. 3 to produce a desired heating pattern in the tissue, but this is not essential, eg the profile may be square or rectangular as in FIG. 1. Other modifications are possible, eg as described with reference to FIGS. 1 and 2 as regards the length of rod 15, the recessing of the resonator, and the inclusion of magnetic material in overlying layer 17, which in FIGS. 3 and 4 contains only dielectric material.

In use, the surface of the overlying layer may either be placed in direct contact with the skin, or a layer of suitable material, eg distilled water in a flexible container (known per se and termed a water bolus), may be interposed between it and the skin. Such a bolus can combine the functions of impedance-matching ($\epsilon$ for distilled water $\approx 80$), conforming to irregular body contours to avoid air-gaps, containing near-field effects and providing surface cooling to prevent the risk of skin burning.

Experimental applicators having the following dimensions etc have been produced:

|  | Half-wave[1] Resonator | Quarter-wave[2] Resonator |
| --- | --- | --- |
| Dielectric material ($\xi$) | 30 | 30 |
| Magnetic material ($\mu$ effective, ie calculated from resonant frequency) | 3.4 | 2.5 |
| Resonator 1, 11 (length, cm) | 7.7 ($\times$ 7.7 wide) | 7.5 ($\times$ 7.5 wide at broad end) |
| Resonator 1, 11 (thickness, mm) | 0.25 | 0.25 |
| Substrate 2, 12 (length, cm) | 16 ($\times$ 15 wide) | 15 (square) |
| Substrate 2, 12 (thickness, cm) | 2.2 | 2.2 |
| Overlayer 7, 17 (thickness, cm) | 2.2 | 2.2 |
| Resonant frequency (MHz) | 190 | 120 |

[1]Substrate similar to FIGS. 1 and 2 but using four ferrite rods (Neosid F29, 8 mm diameter) in two layers located between adjacent slabs of dielectric material (Emerson and Cuming HIK 500F). Non-recesssed resonator, peripheral air-gap unfilled, no ferrite in overlying layer of same dielectric material.
[2]Substrate similar to FIGS. 3 and 4, using single ferrite rod and dielectric material as specified in (1) above. Non-recessed resonator, peripheral air-gap unfilled, no ferrite in overlying layer of same dielectric material.

By way of comparison, at the stated resonant frequencies the expected resonator lengths in the absence of magnetic material in the substrates, ie reduced by the $\epsilon$-value of the dielectric material alone, would be about 14.4 cm in the half-wave case and about 11.4 cm in the quarter-wave case, reductions of approximately 47% and 33% respectively.

With the above examples it was found desirable in use to include a matching water bolus, suitably 2.5 to 5 cm thick, between the overlying layer 7 or 17 and the tissue surface, in order to ensure a far-field wave pattern at the tissue surface and thus avoid hot spots which can arise from near-field heating. The distance at which far-field conditions develop increases with wavelength. By using such a bolus, the production of these conditions need not rely upon the thickness of the overlying layer alone.

The design of other embodiments to meet particular requirements is most easily done by experiment, calculation of the dimensions, etc being difficult.

Figure 5:
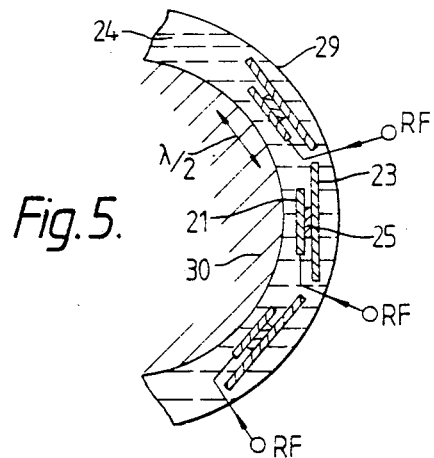
FIG. 5 is a cross-section of an applicator arrangement using a still further embodiment of the invention.

FIG. 5 shows an arrangement for heating a large area of human tissue. A flexible annular vessel 29, eg made of a rubber or plastics material, is arranged to surround and contact the tissue 30 of the patient's body. The vessel 29 is filled with distilled water 24 which acts as the dielectric material ($\epsilon \approx 80, \mu = 1$). Immersed in the water and spaced from the vessel wall by means not shown is a plurality of half-wave metal-plate resonators 21, to which feed connections are taken through the vessel wall, and close to the wall or in contact therewith are mounted metal plates 23, each opposite a plate 21 and having approximately twice the linear dimensions. Between the central region of each plate 21 and the opposite plate 23 is mounted a strip 25 of magnetic material shown end-on. (A similar strip of magnetic material may be located on the opposite face of each plate 21 in register with the strip 25 to enhance the size-reduction effect.) Each plate 21, plate 23 and strip 25 can be mounted in a suitable frame. This arrangement is electrically similar to the microstrip patch applicator of FIGS. 1 and 2 with plates 21 and 23 corresponding to the resonant patch 1 and the ground-plane 3 respectively, the water 24 to the dielectric material 4, and the strips 25 to the magnetic material 5. Between the resonators 21 and the tissue 30, the water 24 provides a reasonable degree of matching. The water can be circulated for cooling purposes, and in effect acts as a bolus.

I claim:

1. An electromagnetic medical applicator comprising:
   a laminar resonator, a conducting ground plane, a layer of an electromagnetic medium separating said resonator from said ground plane, and electrical connection means to said resonator and ground plane, said electromagnetic medium comprising separate volumes of magnetic material and of dielectric material with magnetic material located substantially only adjacent that region of the resonator where in use the resonator current is a maximum and said resonator being in intimate contact with said dielectric material adjacent that region of the resonator where in use the resonator current is a minimum, said magnetic material providing an improved path for the magnetic field associated with said current;
   and a layer comprising at least dielectric material overlying said resonator.

2. An applicator as claimed in claim 1 wherein the resonator is a patch resonator on a solid substrate constituting said electromagnetic medium and backed by said conducting ground-plane, with said magnetic material extending transversely to the polarisation direction of the resonator.

3. An applicator as claimed in claim 2 wherein the resonator is a half-wave patch resonator and said magnetic material underlies the central region of the resonator.

4. An applicator as claimed in claim 3 wherein the layer of dielectric material overlying the resonator has an $\epsilon$-value which approximately matches that of tissue at the resonator frequency.

5. An applicator as claimed in claim 4 wherein the dielectric material of the substrate has approximately the same $\epsilon$-value as said overlying layer.

6. An applicator as claimed in claim 1 wherein the resonator is a half-wave patch resonator and said magnetic material underlies the central region of the resonator.

7. An applicator as claimed in claim 6 wherein the layer of dielectric material overlying the resonator has an $\epsilon$-value which approximately matches that of tissue at the resonant frequency.

8. An applicator as claimed in claim 7 wherein the dielectric material of the electromagnetic medium has approximately the same $\epsilon$-value as said overlying layer.

9. An applicator as claimed in claim 1 wherein the resonator is a quarter-wave patch resonator and said magnetic material underlies one end of the resonator.

10. An applicator as claimed in claim 9 wherein the layer of dielectric material overlying the resonator has an $\epsilon$-value which approximately matches that of tissue at the resonant frequency.

11. An applicator as claimed in claim 10 wherein the dielectric material of the electromagnetic medium has approximately the same $\epsilon$-value as said overlying layer.

12. An applicator as claimed in claim 2 wherein the resonator is a quarter-wave patch resonator and magnetic material underlies one end of the resonator.

13. An applicator as claimed in claim 12 wherein the layer of dielectric material overlying the resonator has an $\epsilon$-value which approximately matches that of tissue at the resonant frequency.

14. An applicator as claimed in claim 13 wherein the dielectric material of the substrate has approximately the same $\epsilon$-value as said overlying layer.

* * * * *